United States Patent
Ishige

(10) Patent No.: US 12,121,345 B2
(45) Date of Patent: Oct. 22, 2024

(54) LENGTH MEASURING APPARATUS, LENGTH MEASURING METHOD, NON-TRANSITORY COMPUTER-READABLE RECORDING MEDIUM, AND HEIGHT SCALE

(71) Applicant: TANITA CORPORATION, Tokyo (JP)

(72) Inventor: Tadaaki Ishige, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 837 days.

(21) Appl. No.: 17/272,161

(22) PCT Filed: Aug. 26, 2019

(86) PCT No.: PCT/JP2019/033367
§ 371 (c)(1),
(2) Date: Feb. 26, 2021

(87) PCT Pub. No.: WO2020/045366
PCT Pub. Date: Mar. 5, 2020

(65) Prior Publication Data
US 2021/0212599 A1      Jul. 15, 2021

(30) Foreign Application Priority Data

Aug. 31, 2018   (JP) .................. 2018-163520

(51) Int. Cl.
*A61B 5/107* (2006.01)
*G01B 11/06* (2006.01)

(52) U.S. Cl.
CPC .......... *A61B 5/1072* (2013.01); *A61B 5/1079* (2013.01); *G01B 11/0608* (2013.01)

(58) Field of Classification Search
CPC ... A61B 5/1072; A61B 5/1079; G01B 11/002; G01B 11/0608; G01B 5/061; G01B 3/10;
(Continued)

(56) References Cited

U.S. PATENT DOCUMENTS 8,109,008 B1 *   2/2012   Niemczak ............ A61B 5/1079
                                                                    600/587
8,408,476 B2      4/2013   Sun et al.
(Continued)

FOREIGN PATENT DOCUMENTS

CN       102451007 A  *   5/2012
CN       103968926 A       8/2014
(Continued)

OTHER PUBLICATIONS

International Search Report issued in PCT/JP2019/033367; mailed Oct. 15, 2019.

*Primary Examiner* — Michael P Stafira
(74) *Attorney, Agent, or Firm* — Studebaker & Brackett PC

(57) ABSTRACT

A length measuring apparatus for measuring length of a measuring object, includes a scale part provided to the measuring object, the scale part having two-dimensional codes with different patterns provided alongside at least in a longitudinal direction; a reading unit configured to read the two-dimensional codes; an obtaining unit configured to obtain coordinate information based on the two-dimensional code; and a conversion unit configured to convert the obtained coordinate information to length information based on a previously generated correspondence between the coordinate information and length information of the measuring object.

10 Claims, 12 Drawing Sheets

(58) Field of Classification Search
CPC .................... G01B 11/00; G01B 11/02; G01B 2003/1023; G01B 2003/1076; G01B 3/1069; G01B 3/1084; G01B 3/1089; G01B 3/1092; G01B 3/1094; G01B 5/004
See application file for complete search history.

(56) References Cited

U.S. PATENT DOCUMENTS

| 9,316,475 | B2 * | 4/2016 | Liu | ...................... A61B 5/1072 |
|---|---|---|---|---|
| 2016/0242676 | A1 * | 8/2016 | Grossmann | .......... A61B 5/7257 |
| 2018/0035655 | A1 | 2/2018 | Callingham | |

FOREIGN PATENT DOCUMENTS

| CN | 108420431 | A | * | 8/2018 | | |
|---|---|---|---|---|---|---|
| DE | 202004017246 | U1 | * | 3/2005 | ............. | G01B 5/004 |
| DE | 202016106704 | U1 | * | 1/2017 | ......... | G01B 11/0608 |
| FR | 3012596 | A1 | * | 5/2015 | ........... | A61B 5/1072 |
| JP | H08336510 | A | * | 12/1996 | | |
| JP | 2006085679 | A | * | 3/2006 | | |
| JP | 2017081012 | A | * | 5/2017 | | |
| JP | 2018-507710 | A | | 3/2018 | | |
| KR | 101322644 | B1 | * | 10/2013 | | |
| WO | WO-2018104994 | A1 | * | 6/2018 | ............... | G01B 3/10 |

\* cited by examiner

LENGTH MEASURING APPARATUS, LENGTH MEASURING METHOD, NON-TRANSITORY COMPUTER-READABLE RECORDING MEDIUM, AND HEIGHT SCALE

TECHNICAL FIELD

The present invention relates to a length measuring apparatus, a length measuring method, a non-transitory computer-readable recording medium, and a height scale including a length measuring apparatus.

BACKGROUND ART

A height scale for measuring height is one of length measuring apparatuses. Conventionally, a digital height scale that does not require an operator to read the scale directly has been proposed. As an example of a digital height scale, a height scale, which counts the number of slits using an optical sensor such as a linear encoder or a rotary encoder when a cursor is moved and converts the number of slits to length, is known.

The inventor of the present invention has recognized that with the method of converting the number of slits to length, the measured value deviates when slit skipping or the like occurs and there is a possibility that height cannot be accurately measured. Further, the inventor of the present invention has recognized that once slit skipping or the like occurs, the measured value continues to deviate in the subsequent measurement, and since the occurrence of slip skipping or the like is difficult to be noticed by the measurement operator, it is necessary to move the cursor to the origin every time height is measured.

JP08-336510A discloses a digital height scale including a scale on which a scale is displayed by a bar code, a sensor provided on a cursor which contacts a head of an object person to read the bar code of the scale, and a liquid crystal display displaying the value of the bar code read by the sensor. In this digital height scale, since the sensor simply reads the bar code at the position where the cursor stops, no slit skipping occurs and the cursor does not need to be moved to the origin every time height is measured.

SUMMARY OF INVENTION

However, in the height scale of JP08-336510A, since the scale is displayed by the bar code instead of a numeric value, the bar code indicating the numeric value must be provided at a position corresponding to the height. Therefore, it is required to mount the scale with high accuracy.

It is an object to accurately measure the length of a measuring object regardless of the accuracy with which a scale part is mounted.

According to an aspect of the present invention, a length measuring apparatus for measuring length of a measuring object, includes a scale part provided to the measuring object, the scale part having two-dimensional codes with different patterns provided alongside at least in a longitudinal direction; a reading unit configured to read the two-dimensional codes; an obtaining unit configured to obtain coordinate information based on the two-dimensional code; and a conversion unit configured to convert the obtained coordinate information to length information based on a previously generated correspondence between the coordinate information and length information of the measuring object.

In the above aspect, the reading unit reads the two-dimensional codes provided alongside on the scale part, and obtains the coordinate information of the two-dimensional code which is read. The coordinate information is converted to the length information based on the correspondence between the previously generated coordinate information and the length information of the measuring object. The two-dimensional code simply indicates the coordinate information on the scale part, and the coordinate information does not indicate the length of the measuring object itself. Therefore, the length of the measuring object can be accurately measured regardless of the mounting accuracy of the scale part.

DESCRIPTION OF EMBODIMENTS

Hereinafter, a length measuring apparatus 10 according to an embodiment of the present invention and a height scale 100 including the length measuring apparatus 10 will be described with reference to the accompanying drawings.

First, referring to FIG. 1, the overall configuration of the height scale 100 will be described.

Figure 1:
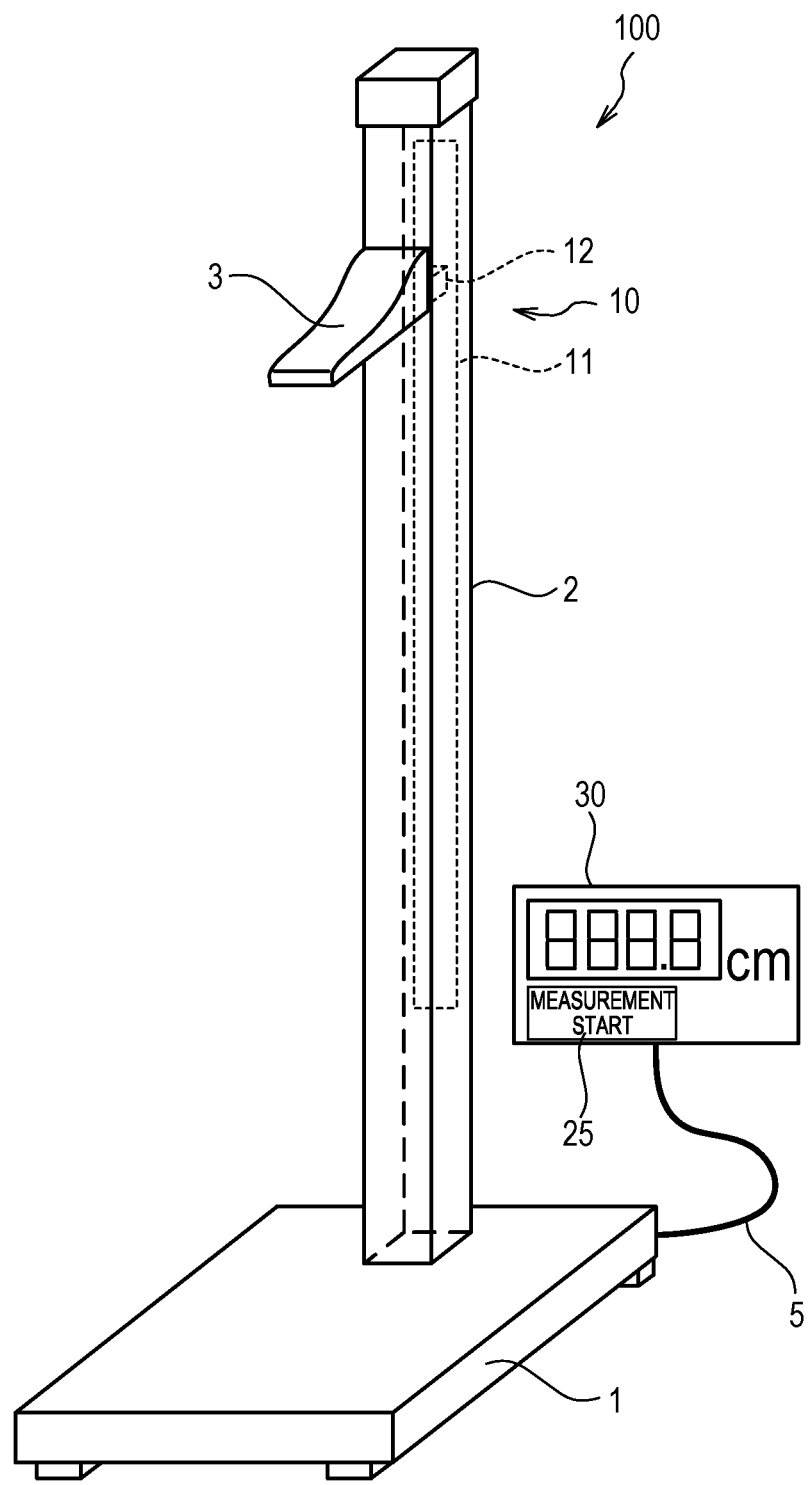
FIG. 1 is a schematic perspective view of a length measuring apparatus according to an embodiment of the present invention and a height scale to which the length measuring apparatus is applied.

As shown in FIG. 1, the height scale 100 includes a measuring base 1, a column 2, a cursor 3, and the length measuring apparatus 10. The length measuring apparatus 10 includes a measurement start switch 25 and a display unit 30, as will be described later.

The measuring base 1 is a platform on which an object person gets during height measurement. The measuring base 1 is placed on a level floor. An upper surface of the measuring base 1 is provided parallel to the floor surface.

The column 2 extends vertically from the measuring base 1. The column 2 is formed in a hollowed shape. A scale part 11, which will be described later, is provided inside the column 2.

The cursor 3 is provided so as to move vertically with respect to the column 2. The cursor 3 projects outwardly from the column 2 so that the lower surface is parallel to the upper surface of the measuring base 1. The cursor 3 is driven by an electric motor (not shown). The cursor 3 automatically moves with respect to the column 2 during height measurement. The cursor 3 is provided with a camera 12 as a reading unit to be described later. The camera captures an image of the scale part 11.

When the measurement start switch 25 is operated while the object person is on the measuring base 1, the height scale 100 moves down the cursor 3 from above. The height scale 100 displays the position of the cursor 3 when contacting an upper end of a head of the object person, that is, the length of the column 2 in the section from the upper surface of the measuring base 1 to the lower surface of the cursor 3 at this time, on the display unit 30 as the height of the object person. Thus, the height scale 100 measures the length of the column 2 from the measuring base 1 which is equivalent to the height of the object person. Here, the column 2 corresponds to measuring object.

When the cursor 3 contacts the head of the object person and the height measurement is completed, the cursor 3 moves up. This allows the object person to get off the measuring base 1.

Next, referring to FIG. 2 to FIG. 6, the length measuring apparatus 10 will be described.

Figure 2:
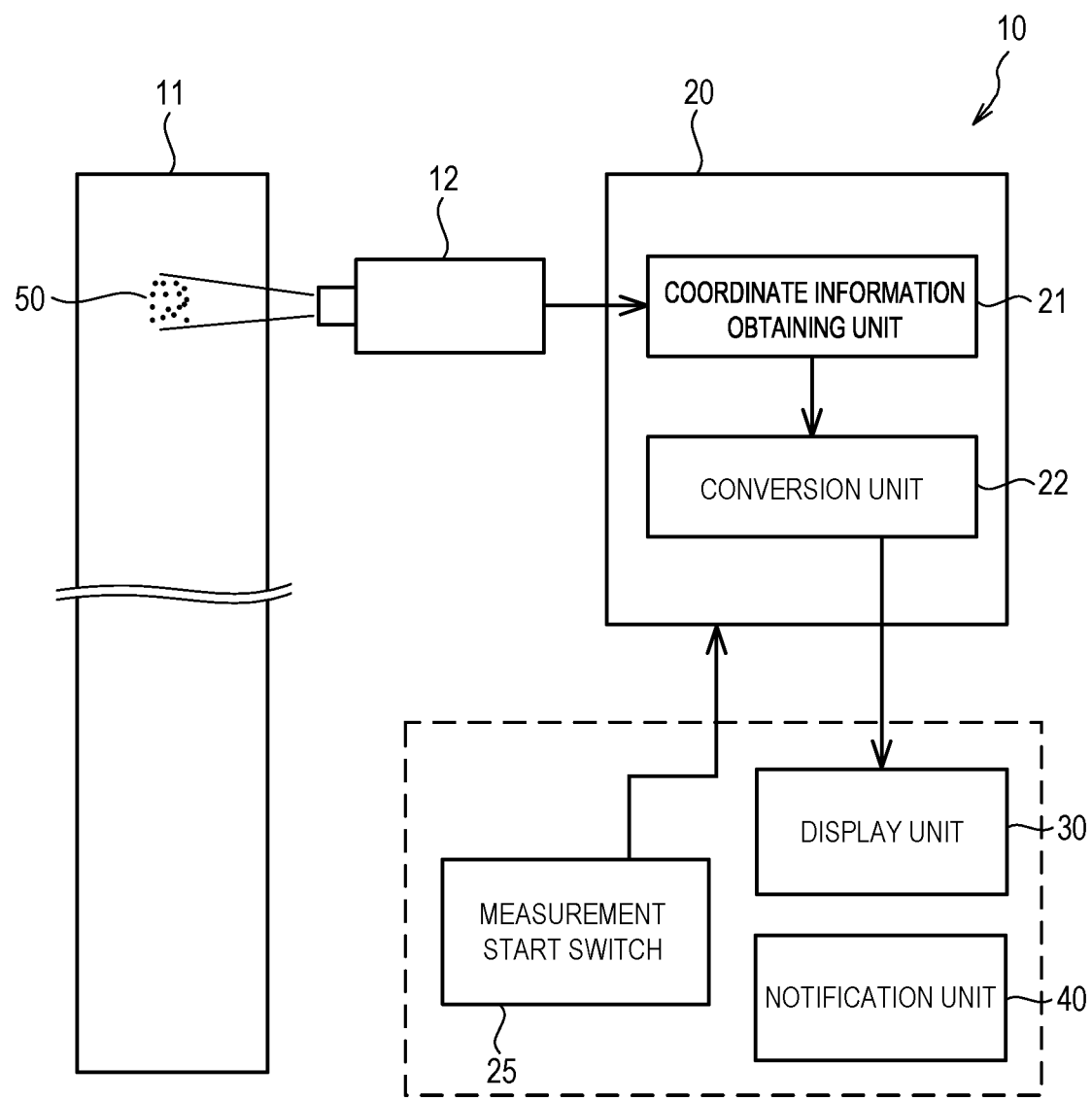
FIG. 2 is a block diagram of the length measuring apparatus.

The length measuring apparatus 10 measures the height of the object person by measuring the length of the column 2 from the upper surface of the measuring base 1. As shown in FIG. 2, the length measuring apparatus 10 includes the scale part 11, the camera 12, a controller 20, the measurement start switch 25, the display unit 30, and a notification unit 40.

Figure 3:
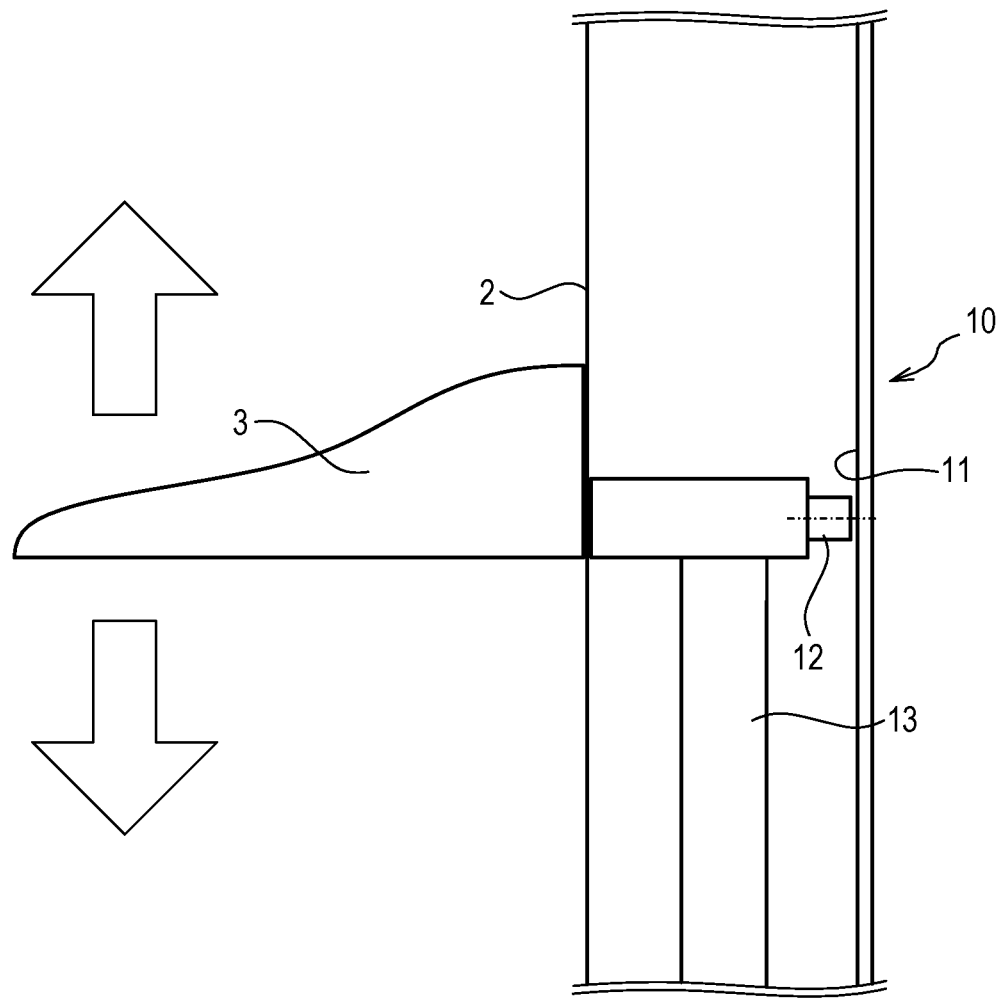
FIG. 3 is an enlarged view illustrating the configuration of the length measuring apparatus.
Figure 4:
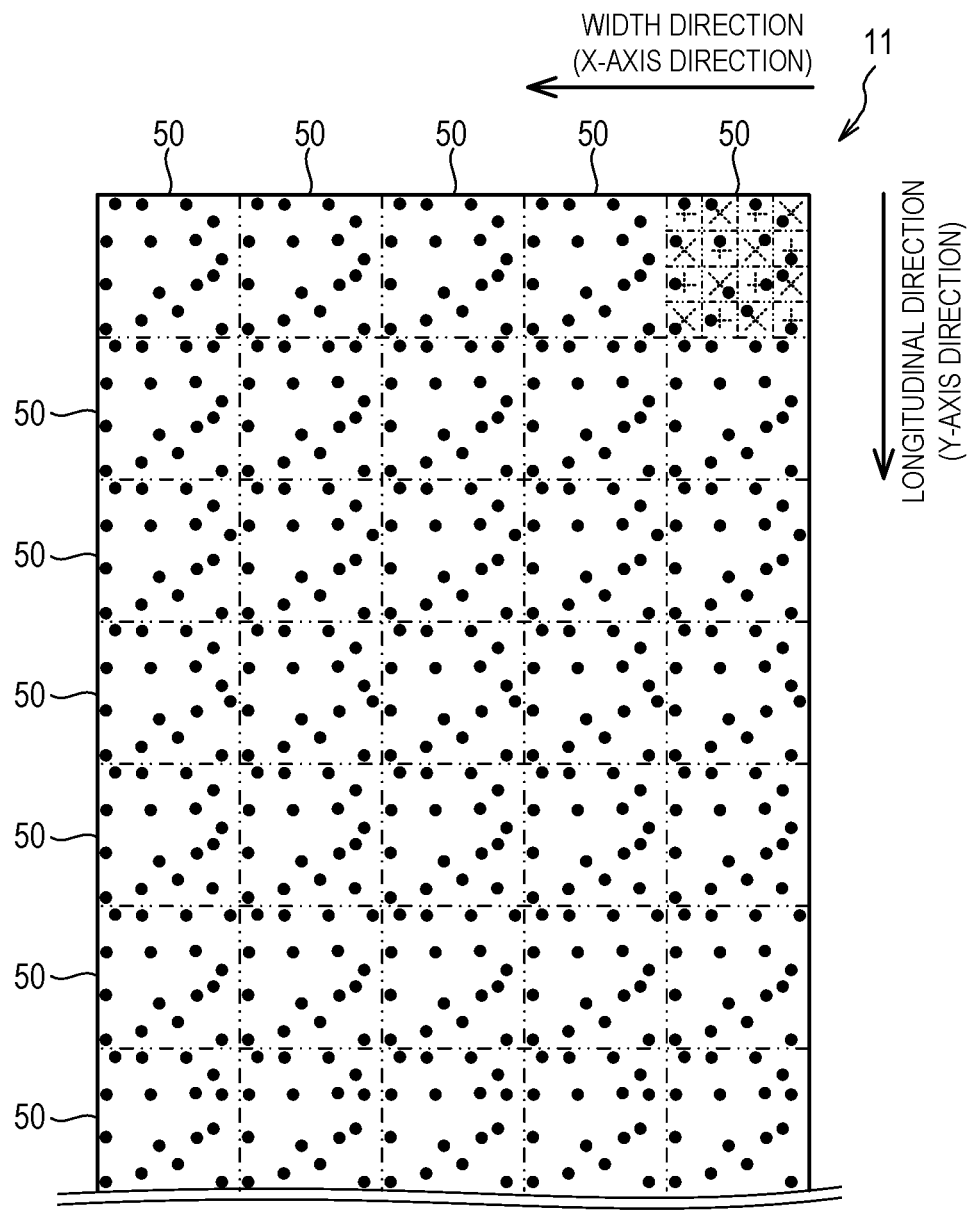
FIG. 4 is a diagram showing an exemplary of two-dimensional codes.

As shown in FIG. 3, the scale part 11 is provided inside the column 2. The scale part 11 is provided so that its longitudinal direction is along the direction of the length to be measured at the column 2 (the longitudinal direction of the column 2). As shown in FIG. 4, the scale part 11 is provided with two-dimensional codes 50 with different patterns. The two-dimensional codes 50 are provided in matrix in the longitudinal direction (Y-axis direction) and in the width direction (X-axis direction) perpendicular to the longitudinal direction. The two-dimensional codes 50 do not necessarily need to be provided in the width direction. The two-dimensional codes 50 may be provided alongside at least in the longitudinal direction.

The scale part 11 is formed to be longer than the measuring range of the length measuring apparatus 10 (the height scale 100 in this embodiment). For example, when the measurement range of the height scale 100 is from 100.0 [cm] to 200.0 [cm], the scale part 11 is formed to have length of about 110 [cm], which is longer by 10 [cm] than the measurement range. As a result, a mounting error can be tolerated when the scale part 11 is mounted on the column 2 and the mounting operation becomes easy.

The two-dimensional codes 50 may be formed in such a manner that it can be read by the camera 12 but is difficult to visually recognize, for example, by being formed in a transparent manner. Therefore, the scale part 11 may be provided on the outer surface of the column 2, and the two-dimensional codes 50 may be formed above a previously applied design or the like.

In FIG. 4, for simplification of explanation, the two-dimensional codes 50 are virtually separated by two-dot chain lines so that the boundaries between adjacent two-dimensional codes 50 are easy to understand. However, in reality, only the two-dimensional codes 50 are displayed on the scale part 11, and the two-dot chain lines are not displayed. The same applies to FIG. 5, FIG. 6 and FIG. 8.

As the two-dimensional codes 50, for example, the two-dimensional codes disclosed in such as JP3706385B, JP4658427B and JP2017-10561A are used. In addition, the present invention is not limited to the above, and it is needless to say that, for example, Zcode (registered trademark) of Toppan TDK Label Co., Ltd. or another conventional two-dimensional codes may be used as the two-dimensional codes 50.

However, the two-dimensional codes 50 used for the length measuring apparatus 10 need to be capable of obtaining coordinate information differing at a predetermined short interval to the extent that the length can be measured by the length measuring apparatus 10. When the length measuring apparatus 10 is used for a height scale, two-dimensional codes capable of obtaining coordinate information differing at least in the longitudinal direction from each other at an interval of, for example, 1 mm or less are used. Hereinafter, the two-dimensional codes 50 used for the length measuring apparatus 10 will be described with reference to the dot pattern disclosed in JP3706385B.

The two-dimensional codes 50 are dot codes indicating coordinate information (X, Y) by the dot pattern. The two-dimensional codes 50 are provided alongside so as to obtain coordinate information differing at an interval of 1 [mm] or less. That is, the two-dimensional codes 50 are formed such that at least coordinate information in the longitudinal direction continuously changes at pitches of 1 [mm] or less when it is read. Here, the two-dimensional codes 50 are provided within an imaginary rectangular area with length of 0.1 [mm] on each side. The two-dimensional codes 50 are successively provided at 0.1 [mm] pitches.

As shown in FIG. 4, the two-dimensional codes 50 are configured by dividing length and width of one pattern into a plurality (here, four), respectively and displaying a dot in each area of a plurality (here, sixteen) of areas. The dot in each area is offset from the center of each area in the vertical, horizontal, or diagonal directions. The two-dimensional code 50 indicates coordinate information (X, Y) according to the difference in the positions of the dots in the respective areas.

In the embodiment shown in FIG. 4, the two-dimensional codes 50 having different patterns corresponding to coordinates in the length direction (Y-axis direction) of the scale part 11 are provided in the length direction (Y-axis direction). In the width direction (X-axis direction) of the scale part 11, the two-dimensional codes 50 having the same patterns are provided.

In this case, since the same two-dimensional codes 50 are aligned in the X-axis direction, even if the imaging area of the camera 12 deviates from a certain row of two-dimensional codes 50 extending in the Y-axis direction, the two-dimensional codes 50 of the adjacent row can be read. The X-coordinates indicated by the two-dimensional codes 50 are the same at any position along the X-axis. Therefore, when the scale part 11 is mounted in parallel with the column 2 or when the scale part 11 is obliquely mounted with a negligible angle, the length can be measured using the Y-coordinate only.

Figure 5:
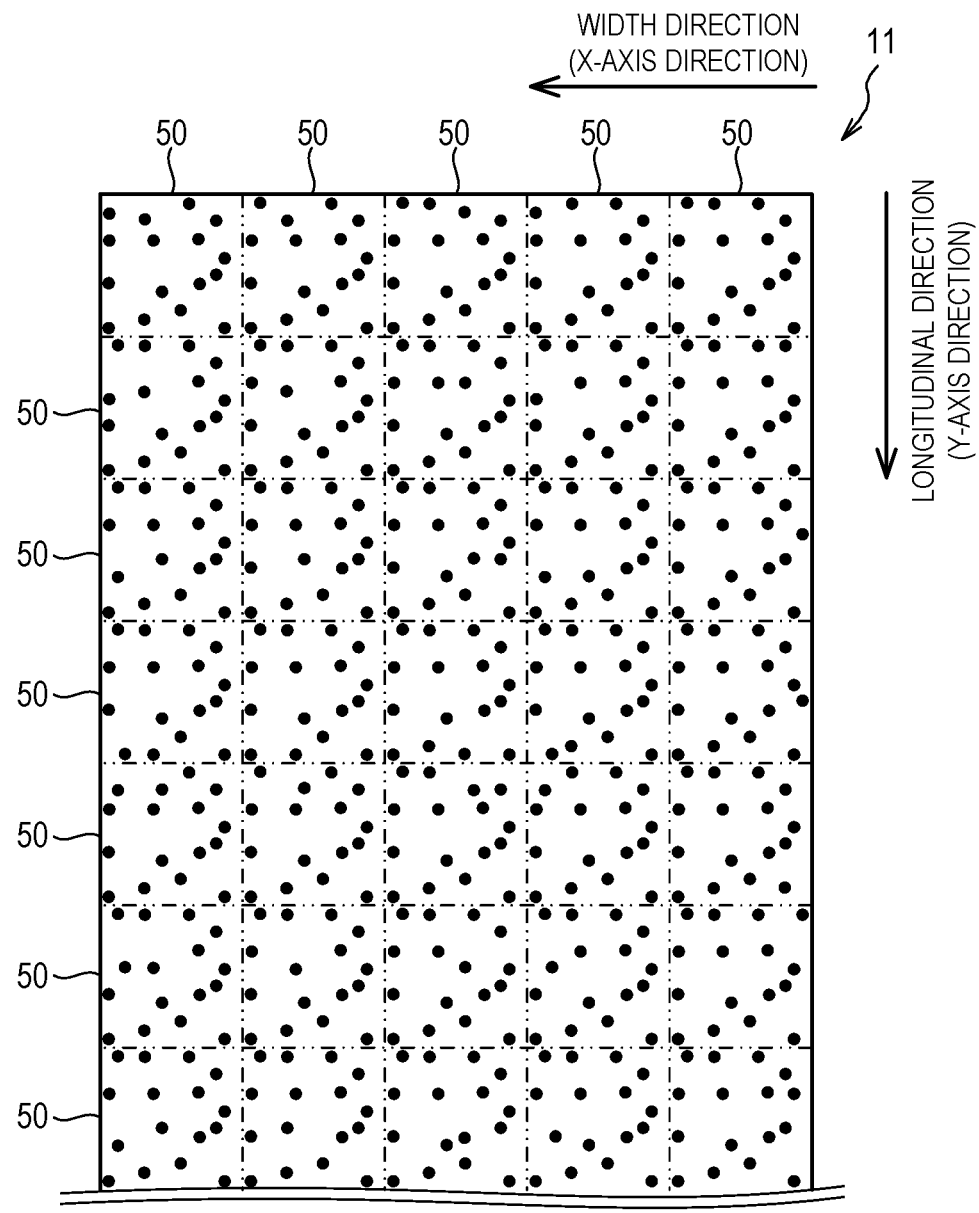
FIG. 5 is a diagram showing a modification of the two-dimensional codes.

Alternatively, as in the modification shown in FIG. 5, the two-dimensional codes 50 having different patterns corresponding to the coordinates in the length direction of the scale part 11 may be provided in the length direction (Y-axis direction), and the two-dimensional codes 50 having different patterns corresponding to the coordinates in the width direction of the scale part 11 may be provided in the width direction (X-axis direction).

In this case, all the two-dimensional codes 50 on the scale part 11 have different coordinates (X, Y). Therefore, if the scale part 11 is attached obliquely to the column 2, i.e. when the direction in which the camera 12 moves is oblique with respect to the length direction of the scale part 11 (Y-axis direction), it is possible to calculate the length using the Pythagorean theorem.

Figure 6:
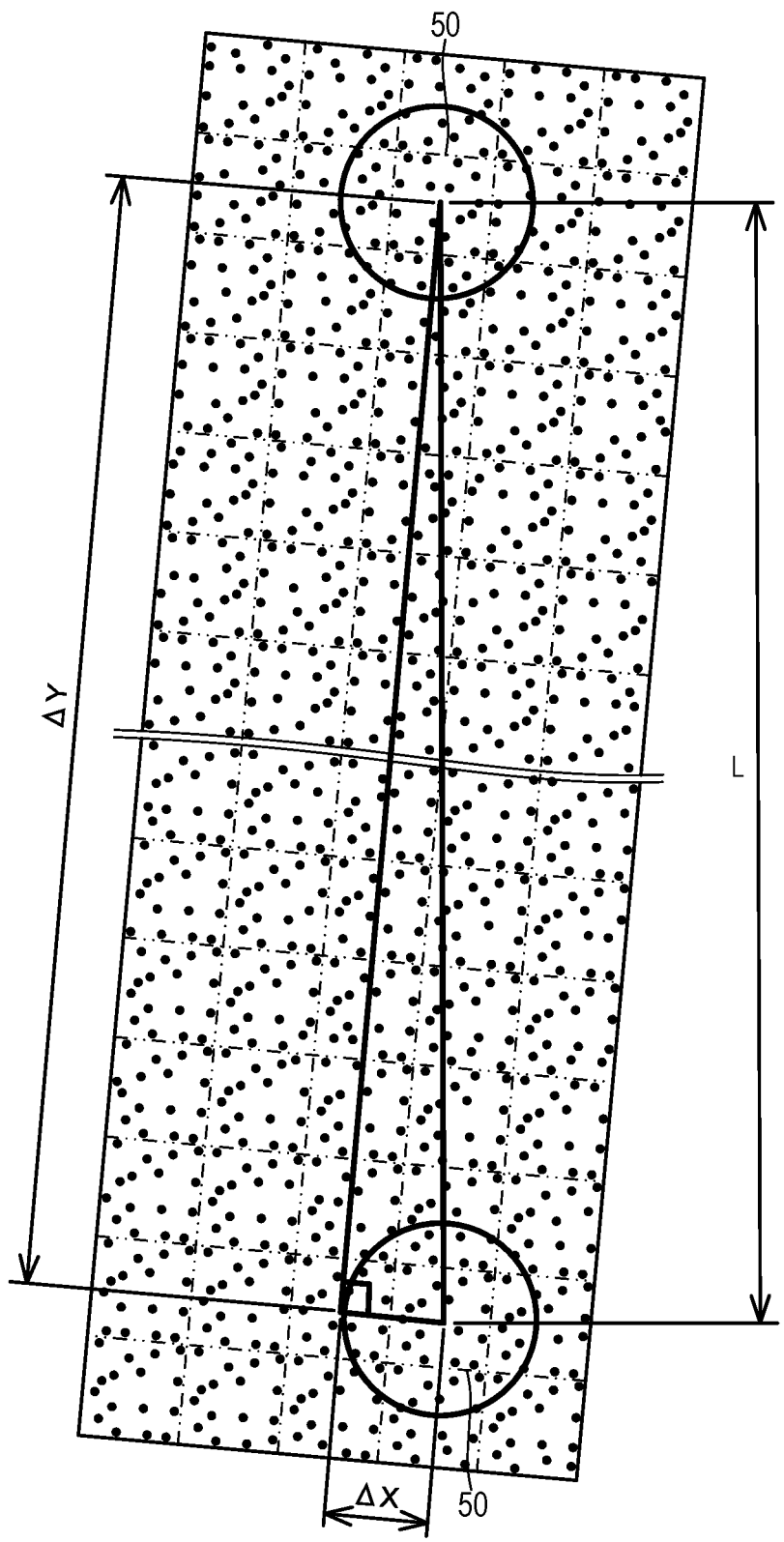
FIG. 6 is a diagram illustrating the measurement of the length when a scale is mounted diagonally.

FIG. 6 shows details. Since the pitch of the two-dimensional codes 50 is 0.1 [mm], the length $\Delta X$ between two points in the X-axis direction and the length $\Delta Y$ between two points in the Y-axis direction are known values. Thus, for example, the length L between the two two-dimensional codes 50 shown in FIG. 6 can be calculated by $\sqrt{(\Delta X^2 + \Delta Y^2)}$.

As shown in FIG. 3, the camera 12 is mounted on the cursor 3 and can move vertically along the column 2 together with the cursor 3. The camera 12 reads the two-dimensional codes 50. An imaging area of the camera 12 is set such that the camera 12 can always read at least one two-dimensional code 50 wherever the cursor 3 is. The camera 12 is connected to the controller 20 via a flexible flat cable 13.

The controller 20 is integrated with the display unit 30, for example. The controller 20 is a microcomputer including a CPU (Central Processing Unit), a ROM (Read Only Memory), a RAM (Random Access Memory), or the like. The controller 20 may be comprised of a plurality of microcomputers. The controller 20 can exhibit various functions in the length measuring apparatus 10 by reading programs stored in the ROM by the CPU.

The controller 20 is programmed to control the length measuring apparatus 10 and the height scale 100. A signal from the camera 12 is input to the controller 20.

As shown in FIG. 2, the controller 20 includes an obtaining unit 21 and a conversion unit 22. The obtaining unit 21 and the conversion unit 22 are virtual units that are not physically present and correspond to functions of the controller 20 for controlling the length measuring apparatus 10 which can be realized by reading the programs stored in the ROM by the CPU. Alternatively, at least one of the obtaining unit 21 and the conversion unit 22 may be physically present using a separate hardware such as ASIC (Application Specific Integrated Circuit).

The obtaining unit 21 obtains coordinate information X and Y from the two-dimensional code 50 read by the camera 12.

The conversion unit 22 holds data indicating the correspondence between the previously generated coordinate information and the length information of the column 2, and converts the coordinate information to the length information based on the data. The conversion unit 22 converts the coordinate information to the length information based on a conversion formula that shows the correspondence between the coordinate information and the length information of the column 2. The conversion formula is generated previously based on the coordinate information and the length information of the column 2.

The correspondence between the coordinate information and the length information of the column 2 is generated with the scale part 11 attached to the column 2. The correspondence between the coordinate information and the length information of the column 2 is generated by reading at least one two-dimensional code 50 corresponding to a known length.

Specifically, the cursor 3 is positioned at a position of, for example, 100.0 [cm], and the coordinate information of the position is read by the camera 12. Then, as the known length, the coordinate information indicated by the pattern of two-dimensional code 50 at the position of 100.0 [cm] from the upper surface of the measuring base 1 is defined as $(X_{100}, Y_{100})$, and the coordinate information indicated by the pattern of the two-dimensional code 50 at any position is defined as $(X_n, Y_n)$. Here, $X_{100}$ and $X_n$ are assumed to have the same X-coordinate. In this case, the conversion formula for obtaining the length $L_n$ [cm] of the column 2 is $L_n = 0.01 \times (Y_n - Y_{100}) + 100.0$.

The constant 0.01 in the above conversion formula is a suitable constant according to the interval at which the coordinate information changes. That is, in the present embodiment, 0.01 is used because the interval is 0.1 [mm], but 0.05 is used when the interval is 0.5 [mm], for example.

Instead, the coordinate information and the length information of the column 2 may be generated by reading two-dimensional codes 50 at two or more places. By doing so, for example, when an error occurs in a print process, a dry process, or the like at 0.1 mm, which is the pitch of the two-dimensional codes 50, the error can be corrected.

Specifically, for example, the coordinate information $(X_{150}, Y_{150})$ indicated by the pattern of the two-dimensional code 50 at the position of 150.0 [cm] is read, and then the coordinate information $(X_{100}, Y_{100})$ indicated by the pattern of the two-dimensional code 50 at the position of 100.0 [cm] is read. Here, $X_{150}$ and $X_{100}$ are assumed to have the same X-coordinate. In this case, the conversion formula for obtaining the length $L_n$ [cm] of the column 2 is $L_n = (150.0 - 100.0) \times (Y_n - Y_{100})/(Y_{150} - Y_{100}) + 100.0$, or $L_n = (150.0 - 100.0) \times (Y_n - Y_{150})/(Y_{150} - Y_{100}) + 150.0$.

The error can be further corrected by reading three or more two-dimensional codes 50 and generating different conversion formulas for each of the scale part 11 areas.

The display unit 30 is provided outside the measuring base 1 and is connected to the controller 20 in the measuring base 1 via a cable 5 (see FIG. 1). The display unit 30 displays and visually notifies the measurement result. The display unit 30 is configured by arranging, for example, four 7-segment displays. The measurement start switch 25 is provided on the outer surface of the display unit 30. Alternatively, the display unit 30 may be configured by a liquid crystal display or the like. In this case, the measurement start switch 25 may be a touch panel in the liquid crystal display.

The notification unit 40 notifies the measurement result by sound. The notification unit 40 notifies the measurement result by reproducing a sound reading a numerical value from a speaker (not shown), for example. At least one of the display unit 30 and the notification unit 40 may be provided. In other words, only one of the display unit 30 and the notification unit 40 may be provided, and both of them may be provided.

Next, mainly referring to FIG. 7 and FIG. 8, height measurement using the height scale 100 will be described.

First, the object person gets on the measuring base 1 and stands upright along the column 2. When the operator operates the measurement start switch 25, the controller 20 executes the flowchart shown in FIG. 7.

In step S11, the controller 20 moves the cursor 3 down from above the object person.

In step S12, it is determined whether or not the cursor 3 has stopped, that is, whether or not the cursor 3 has contacted the upper end of the head of the object person. If it is determined in step S12 that the cursor 3 has stopped, the process proceeds to step S13. On the other hand, when it is determined in step S12 that the cursor 3 has not stopped, the process proceeds to step S11 to move the cursor 3 down more.

In step S13, the controller 20 causes the camera 12 to read the two-dimensional code 50 (reading step, reading procedure).

In step S14, the obtaining unit 21 obtains the coordinate information (X, Y) from the two-dimensional code 50 read in step S13 (obtaining step, obtaining procedure).

In step S15, the conversion unit 22 converts the coordinate information to the length information of the column 2 from the upper surface of the measuring base 1 to the lower surface of the cursor 3 based on the above-described conversion formula (conversion step, conversion procedure).

In step S16, the controller 20 displays the length of the column 2 obtained when the cursor 3 contacts the upper end of the head of the object person on the display unit 30 as the height of the object person.

In step S17, the controller 20 moves the cursor 3 up to the first position because height measurement has been completed.

In this manner, in the height scale 100, the camera 12 reads the two-dimensional codes 50 provided alongside on the scale part 11, and obtain the coordinate information of the two-dimensional code 50. The coordinate information is converted to the length information based on the correspondence between the previously generated coordinate information and the length information of the column 2. Thus, the two-dimensional code 50 simply indicates the coordinate information (information indicating the relative positional relationship) on the scale part 11, and the coordinate information does not indicate the length of the column 2 itself. Therefore, the length of the column 2, i.e., the height of the object person, can be accurately measured regardless of the accuracy with which the scale part 11 is attached to the column 2.

Further, in the height scale 100, the two-dimensional code 50 may be read only at the position where the cursor 3 stops. Therefore, unlike the case of using, for example, a linear encoder or a rotary encoder as disclosed in JP2003-164436A, there is no need to read the two-dimensional code 50 while the cursor 3 is moving. Therefore, the measurement failure caused by slit skipping does not occur.

Figure 7:
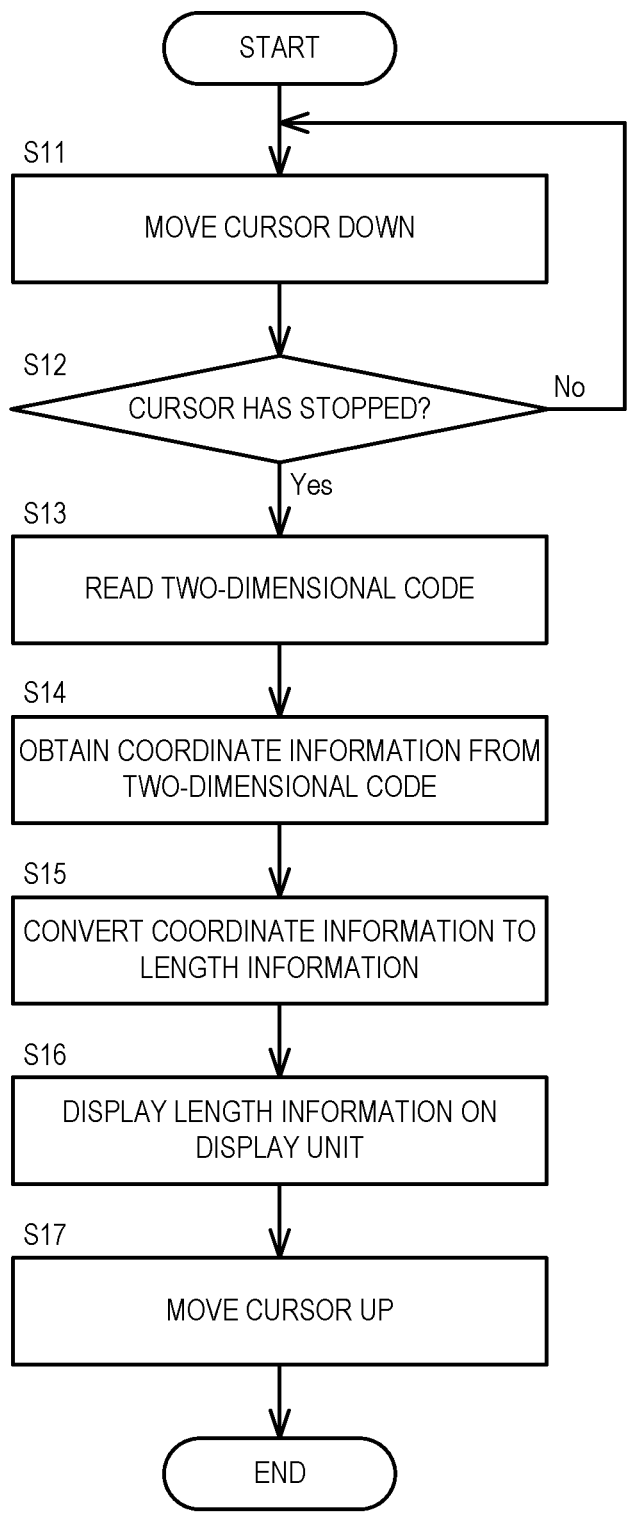
FIG. 7 is a flow chart of measuring height by the height scale.

As a modification of the flow chart shown in FIG. 7, the process may be interrupted when the cursor 3 does not correctly contact the upper end of the head of the object person.

Figure 8:
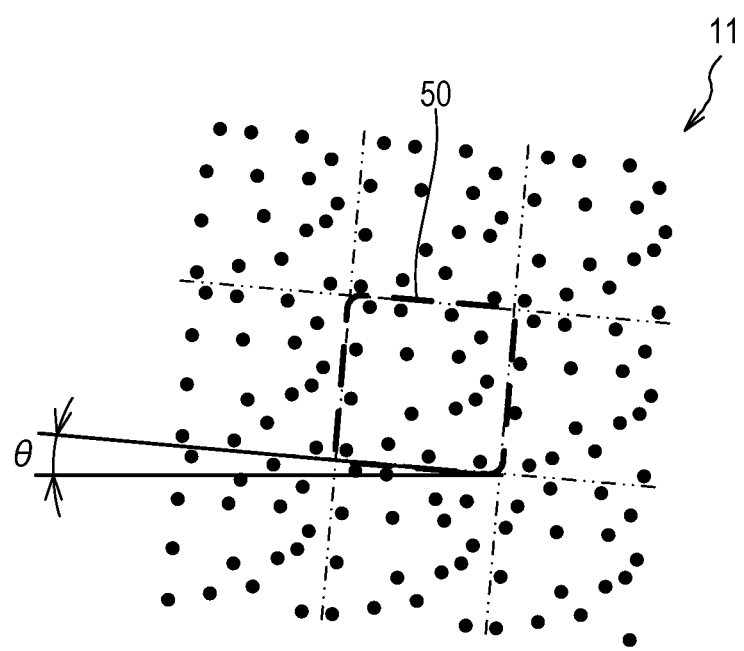
FIG. 8 is a diagram for explaining a rotational angle of the two-dimensional codes.

Specifically, as shown in FIG. 8, when the camera 12 reads the two-dimensional code 50, the rotation angle θ of the two-dimensional code 50 about the rotation axis in a direction perpendicular to the plane, on which the scale part 11 is provided, is read. When the rotational angle θ of the two-dimensional code 50 is larger than a predetermined angle, the cursor 3 may not correctly contact the upper end of the head of the object person. In this case, a warning is displayed on the display unit 30 and the process of the flow chart is interrupted.

According to the above embodiment, the following effects are obtained.

The length measuring apparatus 10 includes the scale part 11 provided at the column 2, to which the two-dimensional codes 50 with different patterns are provided alongside at least in the length direction, the camera 12 for reading the two-dimensional codes 50, the obtaining unit 21 for obtaining the coordinate information from the two-dimensional code 50 which is read, and the conversion unit 22 for converting the obtained coordinate information to the length information based on the correspondence between the previously generated coordinate information and the length information of the column 2.

According to this configuration, in height scale 100, the camera 12 reads the two-dimensional codes 50 provided alongside on the scale part 11, and obtain the coordinate information of the two-dimensional code 50. The coordinate information is converted to the length information based on the correspondence between the previously generated coordinate information and the length information of the column 2. The two-dimensional code 50 simply indicates the coordinate information (information indicating the relative positional relationship) on the scale part 11, and the coordinate information does not indicate the length of the column 2 itself. Therefore, the length of the column 2, i.e., the height of the object person, can be accurately measured regardless of the accuracy with which the scale part 11 is attached to the column 2.

Figure 9:
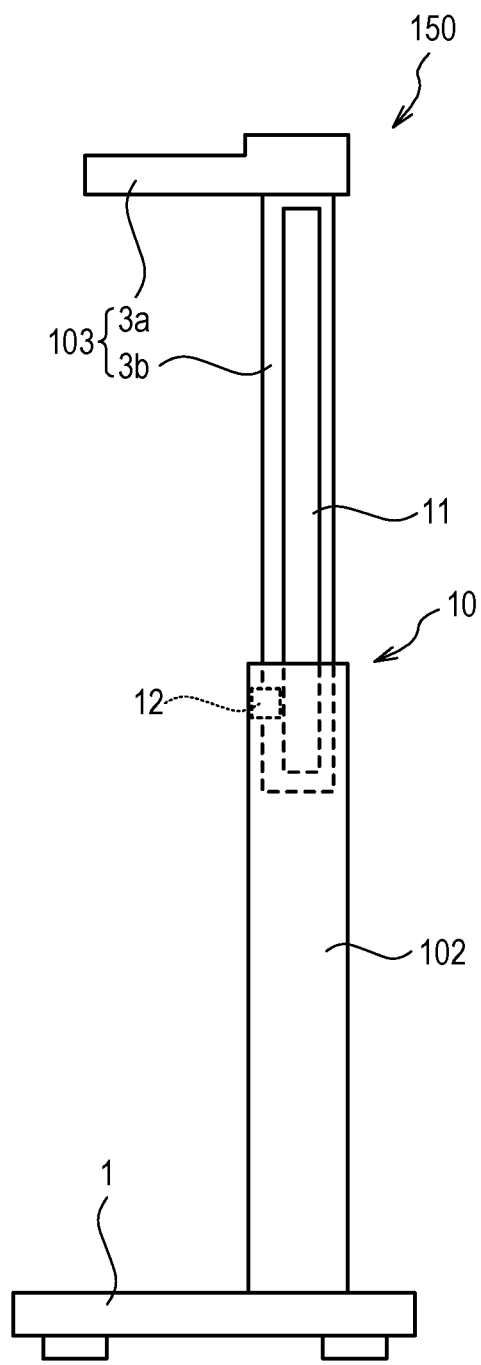
FIG. 9 is a side view illustrating a modification of the height scale.

Next, referring to FIG. 9, a height scale 150 according to a modification of the present embodiment will be described. The following modifications are also within the scope of the present invention, and it is possible to combine the following modifications with the respective configurations of the above-described embodiment, or to combine the following modifications. In each of the modified examples described below, differences from the above-described embodiment are mainly described, and components having similar functions are denoted by the same reference numerals and descriptions thereof are omitted.

The height scale 150 differs from the height scale 100 in that the scale part 11 is provided on the cursor 103 and the camera 12 is provided on a column 102.

The height scale 150 includes the measuring base 1, the column 102, the cursor 103, and the length measuring apparatus 10.

The column 102 extends vertically from the measuring base 1. The column 102 is a hollowed shape. Inside the column 102, the camera 12 capturing the scale part 11 is provided as the reading unit.

The cursor 103 are provided so as to move vertically (in the up and down direction) with respect to the column 102. The cursor 103 includes a cursor body 3a and a movable column 3b.

The cursor body 3a projects outwardly from the movable column 3b such that the lower surface is parallel to the upper surface of the measuring base 1. The cursor body 3a is used to contact the upper end of the head of the object person when height is measured.

The lower end of the movable column 3b is inserted inside the column 102. The movable column 3b is provided so as to move vertically (in the up and down direction) with respect to the column 102. The movable column 3b is provided with the scale part 11.

The height scale 150 also obtains the coordinate information of the two-dimensional code 50 by causing the camera 12 to read the two-dimensional codes 50 provided alongside on the scale part 11. The coordinate information is converted to the length information based on the correspondence between the previously generated coordinate information and the length information of the movable column 3b (the cursor 103). Thus, the two-dimensional code 50 simply indicates the coordinate information on the scale part 11, and the coordinate information does not indicate the length of the movable column 3b itself. Therefore, the length of the movable column 3b, i.e., the height of the object person, can be accurately measured regardless of the mounting accuracy of the scale part 11 on the movable column 3b.

Figure 10:
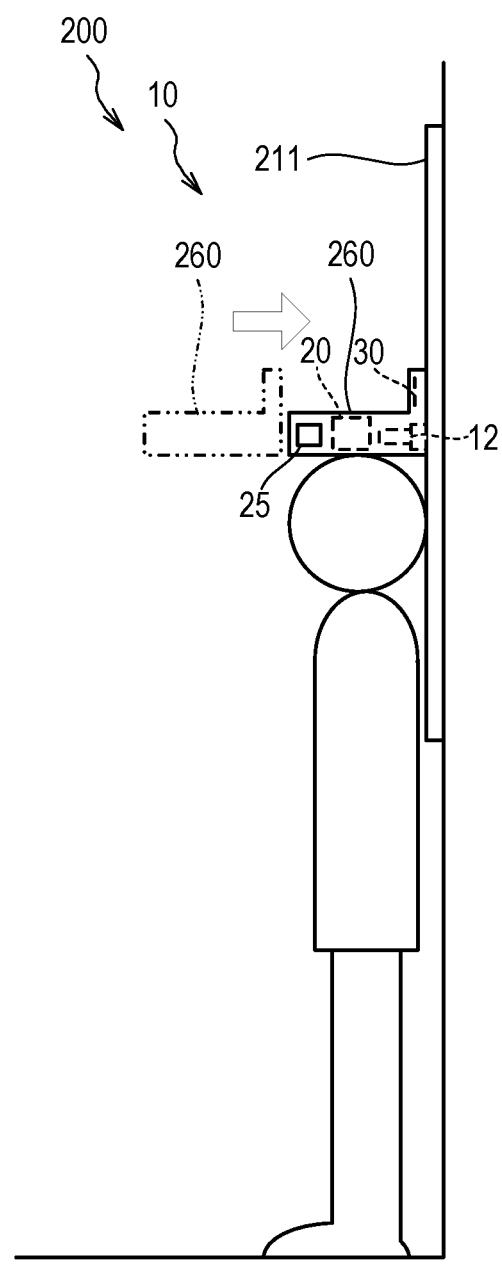
FIG. 10 is a side view illustrating another modification of the height scale.
Figure 11:
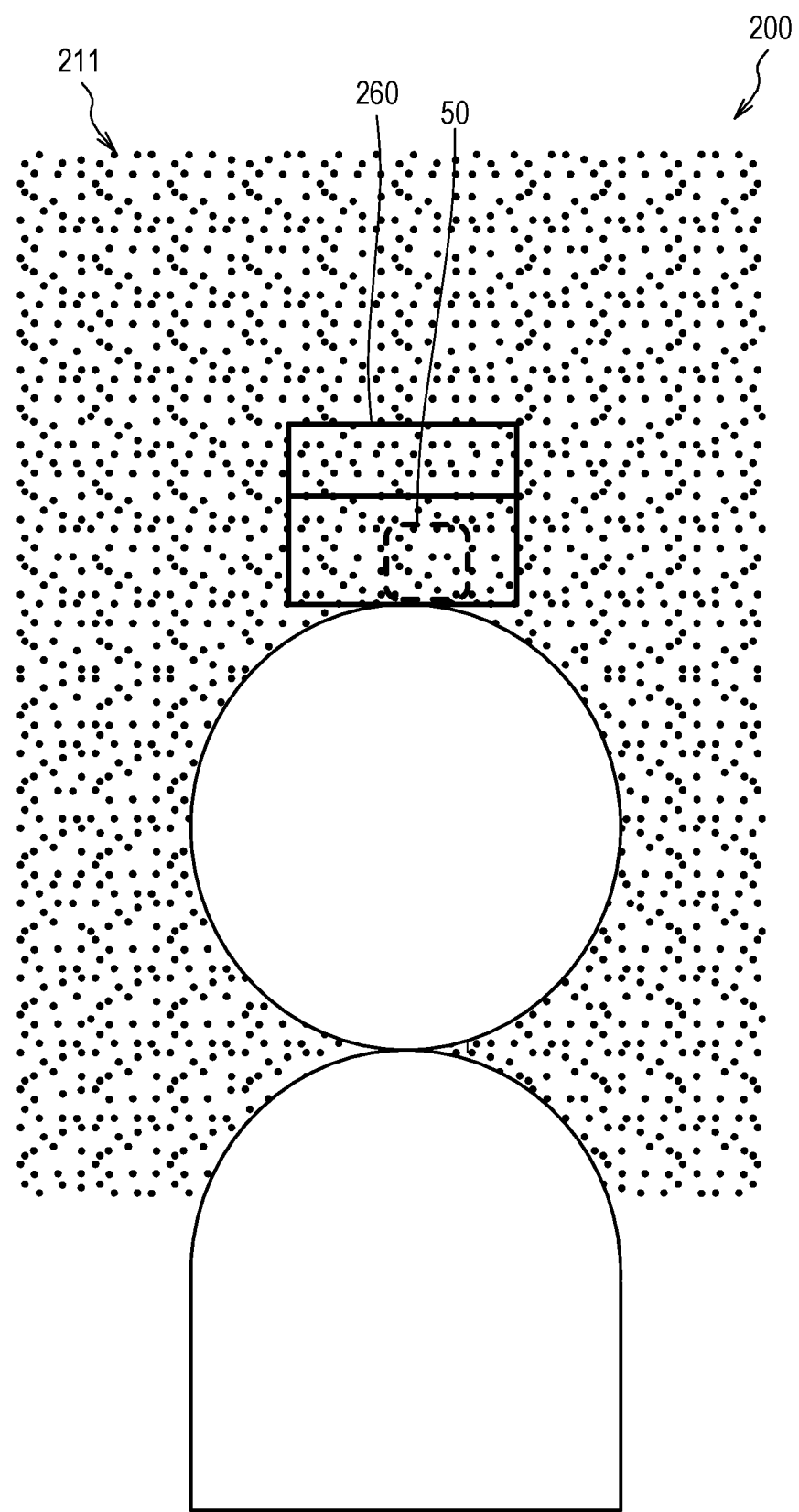
FIG. 11 is a front view in FIG. 10.

Next, referring FIG. 10 and FIG. 11, a height scale 200 according to another modification of the present embodiment will be described.

The height scale 200 differs from the height scale 100 and the height scale 150 in that a scale sheet 211 as a sheet provided with the two-dimensional codes 50 is used.

The height scale 200 includes the length measuring apparatus 10. The length measuring apparatus 10 includes the scale sheet 211 and a reading device 260. In the height scale 200, the scale sheet 211 corresponds to the scale part.

The scale sheet 211 is attached to a vertical plane such as a wall surface or a column. The scale sheet 211 is attached so as to be perpendicular to a floor surface. The scale sheet 211 can be attached at any height position of the wall surface or the column in accordance with the height of the object person.

As described above, the two-dimensional codes 50 can be formed in a manner which is difficult to visually recognize, for example, by forming it into transparent or the like. Therefore, even if the two-dimensional codes 50 are formed on a previously applied design or the like, it can be read by the camera 12. Therefore, as the scale sheet 211, for example, a poster-like paper on which a pattern or a picture is printed can be used.

The reading device 260 includes the camera 12, the controller 20, the measurement start switch 25, and the display unit 30 or the notification unit 40. The reading device 260 is configured to read the two-dimensional code 50 on the scale sheet 211 while being brought into contact with the upper end of the head of the object person.

As a preparation of height measurement, the operator performs an operation to read the two-dimensional code 50 at a predetermined position after attaching the scale sheet 211. By this operation, the conversion formula is generated previously based on the coordinate information and the length information.

Specifically, by using, for example, a ruler, the operator causes the camera 12 to read the coordinate information at a position of 100.0 [cm] from the floor surface. Then, the coordinate information indicated by the pattern of the two-dimensional code 50 at the position of 100.0 [cm] is defined as $(X_{100}, Y_{100})$, and the coordinate information indicated by the pattern of the two-dimensional code 50 at any position is defined as $(X_n, Y_n)$. Here, $X_{100}$ and $X_n$ are assumed to have the same X-coordinate. In this case, the conversion formula for obtaining the length $L_n$ [cm] of the column 2 is $L_n=0.01\times(Y_n-Y_{100})+100.0$.

When height is measured using the height scale 200, the object person stands upright in front of the scale sheet 211 at first. The operator brings the reading device 260 into contact with the upper end of the head of the object person, and operates the measurement start switch 25. When the measurement start switch 25 is operated, the controller 20 performs the processing from step S13 to step S16 of the flowchart in FIG. 7 is executed.

As a result, the height scale 200 also obtains the coordinate information of the two-dimensional code 50 by causing the camera 12 to read the two-dimensional codes 50 provided alongside on the scale sheet 211. The coordinate information is converted to the length information based on the correspondence between the previously generated coordinate information and the height information of the scale sheet 211. Therefore, the height of the object person can be accurately measured.

Further, the height scale 200 can measure height simply by attaching the scale sheet 211 to the wall surface, the column, or the like. Therefore, the scale sheet 211 can be used even if the scale sheet 211 is relocated to another place. In this case, the operator needs to perform the above-mentioned operation for generating the conversion formula after the scale sheet 211 is relocated.

Figure 12:
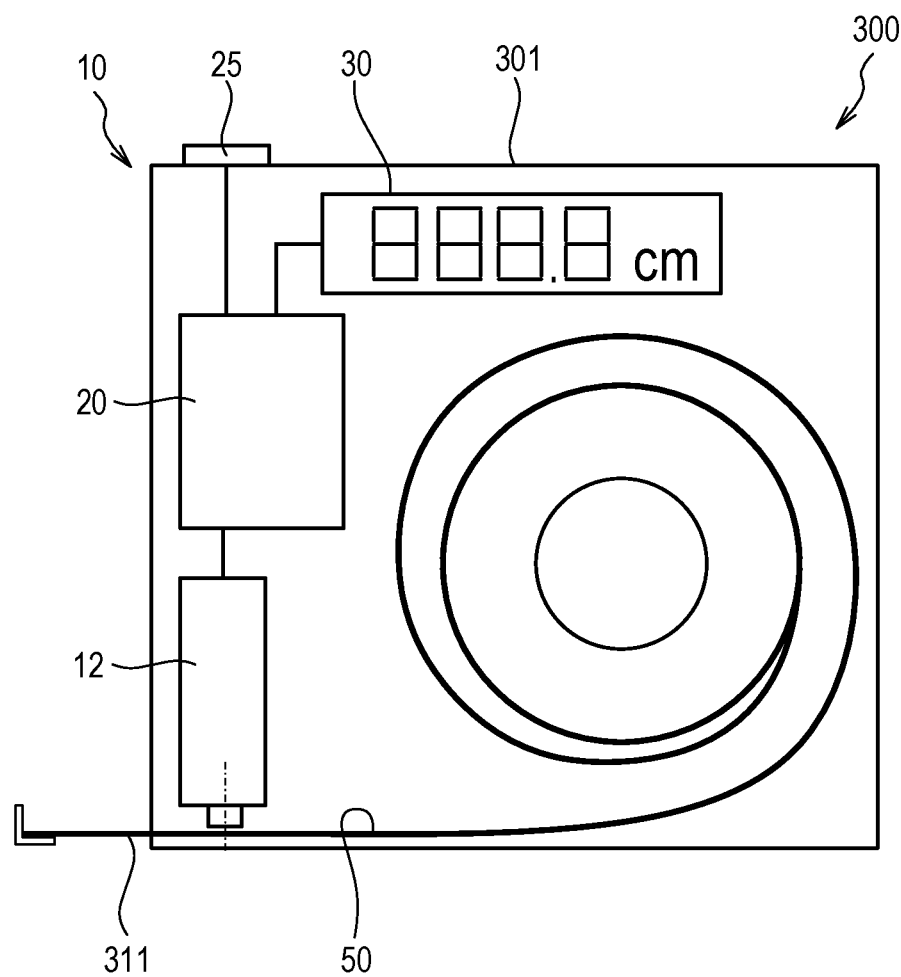
FIG. 12 is a configuration diagram for explaining a modification in which the length measuring apparatus according to the embodiment of the present invention is applied to a tape measure.

Next, referring to FIG. 12, a modification in which the length measuring apparatus 10 is applied to the tape measure 300 will be described.

The tape measure 300 includes a housing 301, a scale part 311, and the length measuring apparatus 10.

The housing 301 accommodates the scale part 311 and the length measuring apparatus 10. The housing 301 is provided with a through hole (not shown) through which the scale part 311 enters and exits, and the display unit 30 for displaying the measurement result.

The scale part 311 is stored in the housing 301 in a wound state. The scale part 311 is biased by a spring (not shown) in a direction to be wound.

The length measuring apparatus 10 includes the camera 12, the controller 20, the measurement start switch 25, and the display unit 30.

As a preparation of height measurement, the operator performs an operation to read the two-dimensional code 50 with the scale part 311 housed in the housing 301. As a result, the conversion formula is generated previously based on the coordinate information and the length information.

Specifically, the operator causes the camera 12 to read coordinate information at a position of 0.0 [cm] where the scale part 311 does not exit the housing 301. Then, the coordinate information indicated by the pattern of two-dimensional code 50 at the position of 0.0 [cm] is defined as $(X_0, Y_0)$, and the coordinate information indicated by the pattern of two-dimensional code 50 at any position is defined as $(X_n, Y_n)$. Here, $X_0$ and $X_n$ are assumed to have the same X-coordinate. In this case, the conversion formula for obtaining the length $L_n$ [cm] of the scale part 311 is $L_n=0.01\times(Y_n-Y_0)$.

When length is measured using the tape measure 300, the operator brings the leading end of the scale part 311 into contact with one end of measuring object, and brings the other end of the measuring object into contact with the end of the housing 301 where the scale part 311 enters and exits. When the operator operates the measurement start switch 25 in this state, the controller 20 performs the processing from step S13 to step S16 of the flowchart in FIG. 7 is executed.

As a result, the tape measure 300 also obtains the coordinate information of the two-dimensional code 50 by causing the camera 12 to read the two-dimensional codes 50 provided alongside on the scale part 311. The coordinate information is converted to the length information based on the correspondence between the previously generated coordinate information and the length information of the scale part 311. Therefore, the length of measuring object can be accurately measured.

Although the embodiments of the present invention have been described in the above, the above-mentioned embodiments merely illustrate a part of application examples of the present invention, and the technical scope of the present invention is not intended to be limited to the specific configurations in the above-mentioned embodiments.

For example, although the single controller 20 is provided in the height scale 100 and the height scale 150 according to the above embodiments, a controller having the obtaining unit 21 may be provided in the cursor 3, and a controller having the conversion unit 22 may be provided separately from the controller provided in the cursor 3. In this case, the coordinate information of the two-dimensional code 50 read by the camera 12 is outputted from the controller in the cursor 3 to the other controller.

In the height scale 100 and the height scale 150 according to the above embodiments, the cursor 3 is moved down automatically, and the position of the cursor 3 when it contacts the upper end of the head of the object person is displayed on the display unit 30 as the height of the object person. Instead, the cursor 3 may be moved manually and the process from step S13 to step S16 in the FIG. 7 may be executed at each time the cursor 3 stops to display the length information of the column 2 on the display unit 30. The same process may be performed in the tape measure 300

The various programs executed by the controller 20 may be programs stored in a non-transitory recording medium such as a CD-ROM, for example.

The present application claims a priority based on Japanese Patent Application No. 2018-163520 filed with the Japan Patent Office on Aug. 31, 2018, the entire contents of which are incorporated into this specification by reference.

DESCRIPTION OF THE REFERENCE NUMERALS 100 height scale
150 height scale
200 height scale
10 length measuring apparatus
1 measuring base
2 column
3 cursor
11 scale part
12 camera (reading unit)
20 controller
21 reading unit
22 conversion unit
50 two-dimensional code
102 column
103 cursor
211 scale sheet (sheet)
311 scale part

The invention claimed is:

1. A length measuring apparatus for measuring length of a measuring object, comprising:
a scale part provided to the measuring object, the scale part having two-dimensional codes with different patterns provided alongside at least in a longitudinal direction;
a reading unit configured to read the two-dimensional codes;
an obtaining unit configured to obtain coordinate information based on the two-dimensional code; and
a conversion unit configured to convert the obtained coordinate information to length information based on a previously generated correspondence between the coordinate information and length information of the measuring object, the correspondence being generated by reading at least one two-dimensional code corresponding to a known length.

2. The length measuring apparatus as defined in claim 1, wherein
the conversion unit configured to convert the coordinate information to the length information based on a conversion formula indicating the correspondence.

3. The length measuring apparatus as defined in claim 1, wherein
the correspondence between the coordinate information and the length information is generated with the scale part attached to the measuring object.

4. The length measuring apparatus as defined in claim 1, wherein
in the longitudinal direction of the scale part, the two-dimensional codes with the different patterns which differ corresponding to coordinates in the longitudinal direction are provided alongside, and
in a width direction perpendicular to the longitudinal direction of the scale part, the two-dimensional codes with same pattern are provided alongside.

5. The length measuring apparatus as defined in claim 1, wherein
in the longitudinal direction of the scale part, the two-dimensional codes with the different patterns which differ corresponding to coordinates in the longitudinal direction are provided alongside, and
in a width direction perpendicular to the longitudinal direction of the scale part, the two-dimensional codes with the different patterns which differ corresponding to coordinates in the width direction are provided alongside.

6. A length measuring method for measuring length of a measuring object, comprising:
a reading step of reading two-dimensional codes, the two-dimensional codes are being provided alongside at least in a longitudinal direction of a scale part provided to a measuring object,
an obtaining step of obtaining coordinate information based on the two-dimensional code; and
a conversion step of converting the obtained coordinate information to length information based on a previously generated correspondence between the coordinate information and length information of the measuring object, the correspondence being generated by reading at least one two-dimensional code corresponding to a known length.

7. A non-transitory computer-readable storage medium storing a program for causing a computer to execute processing comprising:
a reading procedure of reading two-dimensional codes, the two-dimensional codes are being provided alongside at least in a longitudinal direction of a scale part provided to a measuring object,
an obtaining procedure of obtaining coordinate information based on the two-dimensional code; and
a conversion procedure of converting the obtained coordinate information to length information based on a previously generated correspondence between the coordinate information and length information of the measuring object, the correspondence being generated by reading at least one two-dimensional code corresponding to a known length.

8. A height scale with the length measuring apparatus as defined in claim 1, comprising:
a column; and
a cursor provided to move in a vertical direction with respect to the column, wherein
the scale part is provided to one of the column and the cursor such that the longitudinal direction aligns with the vertical direction,
the reading unit is provided to the other one of the column and the cursor, and the scale part is provided with the two-dimensional codes provided alongside such that coordinate information which differs at a predetermined interval in the longitudinal direction.

9. A height scale with the length measuring apparatus as defined in claim 1, wherein the scale part is a sheet on which the two-dimensional codes are provided alongside such that coordinate information which differs at a predetermined interval in the longitudinal direction, and the height scale is provided with a reading device with the reading unit, the reading device is configured to read the two-dimensional codes on the sheet while the reading device contacts an upper end of a head of an object person.

10. A length measuring apparatus for measuring length of a measuring object, comprising:

a scale part provided to the measuring object, the scale part having two-dimensional codes with different patterns provided alongside at least in a longitudinal direction;

a reading unit configured to read the two-dimensional codes;

an obtaining unit configured to obtain coordinate information based on the two-dimensional code; and a conversion unit configured to convert the obtained coordinate information to length information based on a previously generated correspondence between the coordinate information and length information of the measuring object, the correspondence being generated by reading two-dimensional codes corresponding to a known length at two places.

* * * * *